(12) United States Patent
Meudt et al.

(10) Patent No.: US 7,468,460 B2
(45) Date of Patent: Dec. 23, 2008

(54) METHOD FOR PRODUCING AMINES FROM HYDROXAMIC ACIDS

(75) Inventors: Andreas Meudt, Hofheim (DE); Claudius Boehm, Frankfurt am Main (DE)

(73) Assignee: Archimica GmbH, Frankfurt am Main (DE)

( * ) Notice: Subject to any disclaimer, the term of this patent is extended or adjusted under 35 U.S.C. 154(b) by 0 days.

(21) Appl. No.: 11/995,000

(22) PCT Filed: Jul. 5, 2006

(86) PCT No.: PCT/EP2006/006549

§ 371 (c)(1), (2), (4) Date: Jan. 8, 2008

(87) PCT Pub. No.: WO2007/006465

PCT Pub. Date: Jan. 18, 2007

(65) Prior Publication Data

US 2008/0221357 A1    Sep. 11, 2008

(30) Foreign Application Priority Data

Jul. 11, 2005   (DE) .................. 10 2005 032 592

(51) Int. Cl.
  *C07C 261/00* (2006.01)
  *C07C 209/00* (2006.01)
(52) U.S. Cl. ........................ 564/394; 560/24
(58) Field of Classification Search .............. None
  See application file for complete search history.

(56) References Cited

U.S. PATENT DOCUMENTS 5,354,891 A    10/1994   Obayashi

FOREIGN PATENT DOCUMENTS

DE    196 34 446 A1    11/1997

OTHER PUBLICATIONS

T. Isobe et al. "2-Chloro-1,3-dimethylimidazolinium Chloride. 3. Utility for Chlorination, Oxidation Reduction, and Rearrangement Reactions", J.Org.Chem., vol. 64, No. 16, pp. 5832-5835, 1999.
H. R. Snyder et al. "Polyphosphoric acid as a reagent in organic chemistry. IV. Conversion of aromatic acids and their derivatives to amines", J. of Am. Chem. Soc., vol. 75, No. 8, 1953, pp. 2014-2015.

*Primary Examiner*—Samuel A Barts
(74) *Attorney, Agent, or Firm*—ProPat, L.L.C.

(57) ABSTRACT

A method for producing unprotected or carbamate-protected amines of formulae (II) and (III) or $R^1$—$NH_2$ (II) or $R^1$—$NHCO_2R^2$ (III) by reacting hydroxamic acids of formula (I) ($R^1$ CONHOH) with a) alkylpliosphonic acid anhydrite's, b) alcohol $R^2OH$ and c) optionally with a base, at a temperature ranging from 100 to +120°C., wherein the hydroxainic acid (I) is produced prior to or during reacting (in situ) and $R^1$ is an optionally substituted linear or branched $C_1$-$C_{12}$ alkyl radical, substituted $C_3$-$C_{10}$ cycloalkyl, alkenyl, aryl or heteroaryl radical and $R^2$ is an open-chain, cyclic or branched allyl, aryl or $C_1$ to $C_{12}$-alkyl radicals, or aryloxy, allyloxy or alkoxy radical possibly substituted with open-chain, cyclic or branched $C_1$ to $C_{12}$-alkyl radicals.

9 Claims, No Drawings

METHOD FOR PRODUCING AMINES FROM HYDROXAMIC ACIDS

CROSS-REFERENCE TO RELATED APPLICATIONS

This application is being filed under Rule 1.371 as a National Stage Application of pending International Application No. PCT/EP2006/006549 filed Jul. 5, 2006, which claims priority to the following parent application: German Patent Application No. 10 2005 032 592.0, filed Jul. 11, 2005. Both International Application No. PCT/EP2006/006549 and German Patent Application No. 10 2005 032 592.0 are hereby incorporated by reference herein in their entirety.

FIELD OF THE INVENTION

The present invention relates to the production of amines, particularly the production of amines by reacting hydroxamic acids with alkyipliosphonic anhydrides.

BACKGROUND OF THE INVENTION

Amines are important intermediates with extremely diverse possible uses in organic synthesis. The importance in modern organic synthesis is restricted only by limitations in the availability of these classes of compounds. The corresponding carboxylic acids or derivatives thereof are available much more often than the amines, for example as natural products, and therefore all methods for degrading carboxylic acid derivatives to the corresponding amines are per se of great interest. Standard methods for preparing primary amines from carboxylic acids or carboxylic acid derivatives are the Hofmann, Curtius, Schmidt and Lossen degradation reactions.

There is a phenomenal increase in the importance of chemo-, regio- and stereoselective reagents in modern organic synthesis. If, for example, it is wished to convert a particular carboxylic acid group from a complex molecule with numerous functional groups into a primary amine, many of the methods mentioned are unsuitable for selectivity reasons. In addition, azides, hydrazoic acid, bromine or chlorine represent a considerable safety risk.

A highly selective solution to the problem of converting carboxylic acids into primary amines which is applicable also to complex multifunctional molecules often having more than one stereocenter has been lacking to date. Although the known reagents are able to bring about the desired transformations, other groups are often also affected. In many cases, even remote stereocenters are epimerized due to the drastic conditions necessary. In addition, the transformation should be applicable with very mild condition-s, the isolation of the product should be very easy and the removal of the secondary products of the reagent employed should be possible without additional process steps.

It would therefore be very desirable to have a method which is able to convert carboxylic acids by rearrangement into the corresponding primary amines but, at the same time, has very mild reaction conditions and working up which is as simple as possible, and can additionally be employed in commercially useful methods. The known reagents do not solve this problem, as will be demonstrated by some examples: in the Hofmann degradation, carboxamides are degraded by treatment with corrosive and toxic bromine or chlorine and alkali to give the primary amine, with numerous functional groups not being tolerated because of the great reactivity of the halogens employed. In the Curtius degradation, toxic hydrazine or explosive azides are employed, and in the Schmidt degradation toxic hydrazoic acid is employed, the latter likewise being able to cause explosions if not properly handled.

SUMMARY OF ADVANTAGEOUS EMBODIMENTS OF THE INVENTION

It has surprisingly been found that all these problems are solved by reacting hydroxamic acids with alkylphosphonic anhydrides such as, for example, cyclic 2,4,6-substituted 1,3,5,2,4,6-trioxatriphosphinanes, where appropriate in the presence of bases. This combination is a highly selective method for converting carboxylic acids into the corresponding carbamate-protected amines, with simultaneously the desired freedom from epimerization and maximum regio- and stereoselectivity being observed with at the same time virtually quantitative yields.

DETAILED DESCRIPTION OF ADVANTAGEOUS EMBODIMENTS OF TILE INVENTION

The present invention thus relates to a highly selective method for preparing unprotected or carbamate-protected amines of the formulae (II) and (III), $$R^1\text{—}NH_2 \qquad (II)$$

or $$R^1\text{—}NHCO_2R^2 \qquad (III)$$

by reacting hydroxamic acids of the formula (I)

$$(R^1CONHOH) \qquad (I)$$

with
a.) alkylphosphonic anhydrides,
b.) an alcohol $R^2OH$ and
c.) optionally a base at a temperature in the range from −100 to +120° C., where the hydroxamic acid (I) is generated either before the reaction or during the reaction (in situ), and $R^1$ is an optionally substituted linear or branched $C_1$-$C_{12}$-alkyl radical, substituted $C_3$-$C_{10}$-cycloalkyl, alkenyl, aryl or heteroaryl radicals, and $R^2$ is an allyl, aryl, open-chain, cyclic or branched $C_1$ to $C_{12}$-alkyl radical, an aryloxy, allyloxy or alkoxy radical optionally substituted by open-chain, cyclic or branched $C_1$ to $C_{12}$-alkyl radicals.

The hydroxamic acids can either be employed as isolated pure precursors or be generated by a method known to the skilled worker for preparing hydroxamic acids either before the reaction or during the reaction (in situ). This can take place for example by reacting carbonyl halides and hydroxylamine or salts thereof, by reacting carboxylic esters with hydroxylamine or salts thereof, or by reacting free carboxylic acids with hydroxylamine or salts thereof in the presence of dehydrating agents. Owing to the limited commercial availability of hydroxamic acids, it is preferred for them to be generated for example by one of the abovementioned methods and then without delay rearranged according to the invention in the resulting reaction mixture. it is possible in particular starting from carboxylic acids and hydroxylamine for the hydroxamic acid to be formed by a further equivalent of alkylphosphonic anhydride and subsequently to be rearranged by the same reagent.

The alcohols R²OH preferably employed are those in which R² is a methyl, ethyl, n-propyl, isopropyl, n-butyl, 2-butyl, tert-butyl, isobutyl, pentyl, hexyl, phenyl, benzyl, especially a tert-butyl or benzyl substituent.

The amount of alcohol added is generally at least stoichiometric in relation to the starting compound, but may also be above stoichiometric, for example in the ratio 1 hydroxamic acid:1.2 alcohol.

In a preferred embodiment of the invention, the cyclic phosphonic anhydride is a 2,4,6-substituted 1,3,5,2,4,6-trioxatriphosphinane of the formula (IV)

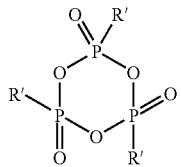

(IV)

in which R' is independently of one another allyl, aryl or open-chain or branched $C_1$ to $C_{12}$-alkyl radicals, in particular $C_1$-$C_8$-alkyl radicals.

Preference is given to use of phosphonic anhydrides of the formula (IV) in which R' is a methyl, ethyl, n-propyl, isopropyl, n-butyl, 2-butyl, isobutyl, pentyl, hexyl, especially an ethyl, propyl and/or butyl radical.

The rearrangement to give unprotected amines (II) or carbamate-protected amines (III) can generally be carried out at temperatures in the range from −100 to +120° C., with preference for temperatures in the range from −30 to +30° C., lower temperatures generally correlating with higher selectivities. The reaction time depends on the temperature used and is generally from 1 to 12 hours, in particular 3 to 6 hours.

The addition of bases, especially amines, is generally unnecessary but may prove advantageous in the individual case. The amount of base added is generally at least stoichiometric in relation to the starting compound, but may also be above stoichiometric, for example in the ratio 1 hydroxamic acid:2 base.

Amines $NR^3_3$ are preferably employed as base, where $R^3$ is an allyl, aryl, open-chair, cyclic or branched $C_1$ to $C_{12}$-alkyl radical, an aryloxy, allyoxy or alkoxy radical, optionally substituted by open-chain, cyclic or branched $C_1$ to $C_{12}$-alkyl radicals, and $R^3$ in $NR^3_3$ may represent different radicals.

$R^3$ is in particular H, methyl, ethyl, n-propyl, isopropyl, n-butyl, 2-butyl, isobutyl, pentyl, hexyl, phenyl, preferably H, ethyl, n-propyl, isopropyl, n-butyl, 2-butyl, isobutyl or phenyl or a combination of said substituents.

The phosphonic anhydride can be added to the reaction medium either as melt or as liquid mixture dissolved in a solvent. Suitable solvents in this connection are those which undergo no side reactions with the phosphonic anhydride, which are all aprotic organic solvents such as, for example, petroleum ether, butane, pentane, hexane, heptane, octane, cyclobutane, cyclopentaner cyclohexane, cycloheptane, cyclooctane, dichloromethane, chloroform, tetrachloromethane, 1,2-dichloroethane, 1,1,2,2-tetrachloroethane, methyl acetate, ethyl acetate, propyl acetate, butyl acetate, dimethylformamide, diethylformamide, dimethylacetamide, diethylacetamide, diethyl ether, diisopropyl ether, tert-butyl methyl ether, THF, dioxane, acetonitrile or mixtures thereof, with particular preference for dichloromethane, chloroform, ethyl acetate, propyl acetate, butyl acetate, dimethylformamide, diethyl-formamide, dimethylacetamide, diethylaceta-mide, diisopropyl ether, tert-butyl methyl ether, THF, dioxane, acetonitrile or mixtures thereof, with very particular preference for dichloromethane, chloroform, ethyl acetate, butyl acetate, dimethylacetamide, tert-butyl methyl ether, THF, dioxane, acetonitrile or mixtures thereof, and with especial preference for THF, ethyl acetate or butyl acetate.

The amount of phosphonic anhydride added is generally at least one third stoichiometric in relation to the hydroxamic acid or to the starting compound for generating the hydroxamic acid, based on P equivalents, but may also be above stoichiometric, for example in the ratio 1 carboxylic acid:3 phosphonic anhydride, preferably 1 carboxylic acid:2 phosphonic anhydride.

The reactions are preferably carried out in such a way that the appropriate hydroxamic acid is introduced into a solvent at the appropriate reaction temperature. The hydroxamic acid is then activated by metering in the phosphonic anhydride as melt or solution, is heated and the desired amine is isolated. Where appropriate, the alcohol is added before the beating, and the desired carbamate-protected amine is isolated.

In a further preferred embodiment of the method of the invention, the appropriate carboxylic ester is introduced with hydroxylamine or a salt of hydroxylamine and a base into a solvent, whereby the hydroxamic acid is initially formed. After it has been ensured by in-process control that formation of the hydroxamic acid is complete, the rearrangement is then carried out as described above.

The reaction product is isolated preferably by hydrolysis and simple phase separation, because the secondary products of the phosphonic anhydrides are generally very soluble in water. Depending on the nature of the product to be isolated, subsequent extractions may also be necessary. The secondary product formed from the phosphonic anhydride ordinarily does not interfere with subsequent reactions, so that direct employment of the reaction solutions obtained often gives very good results too.

All the procedures mentioned are notable for very good yields (typically 90-100%, especially >95%) with simultaneous absence of side reactions and epimerizations. The selectivities of the reaction of the invention are in the region of 99-100%, especially >99.5%.

The method of the invention is to be illustrated by the following examples, without restricting the invention thereto:

EXAMPLES

Example 1

Rearrangement of Benzhydroxamic Acid to tert-butyloxycarbonylaniline 1 mol of benzhydroxamic acid and 2 mol of triethylamine were introduced into 50 ml of ethyl acetate and cooled to 0° C. 1.2 mmol of T3P® solution (T3P® cyclic propanephosphonic anhydride, Clariant GmbH) in ethyl acetate (50% w/w) were metered in while maintaining the reaction temperature, followed by stirring at this temperature for a further three hours. 1.2 mol of tert-butanol were added, and the reaction mixture was stirred at 60° C. for a further hours. At this time, GC of the reactions indicated a conversion of 100%. After warming to room temperature, 180 ml of water were added and the phases were separated. After the solvent had been condensed out, the product remained in a yield of 97%, HPLC purity 98% (a/a).

Example 2

Rearrangement of Benzhydroxamic Acid to benzyloxycarbonylaniline 1 mol of benzhydroxamic acid and 2 mol of triethylamine were introduced into 50 ml of ethyl acetate and cooled to 0° C. 1.2 mol of T3P® solution in ethyl acetate (50% w/w) were metered in while maintaining the reaction temperature, followed by stirring at this temperature for a further three hours. 1.2 mol of benzyl alcohol were added, and the reaction mixture was stirred at 60° C. for a further hour. At this time, GC of the reactions indicated a conversion of 100%. After warming to room temperature, 180 ml of water were added and the phases were separated. After the solvent had been condensed out, the product remained in a yield of 96%, HPLC purity 97% (a/a).

Example 3

Rearrangement of octylhydroxamic Acid to benzyloxycarbonylheptylamine 1 mol of octylhydroxamic acid and 2 mol of triethylamine were introduced into 50 ml of ethyl acetate and cooled to 0° C. 1.2 mol of T3P® (solution in ethyl acetate (50% w/w) were metered in while maintaining the reaction temperature, followed by stirring at this temperature for a further three hours. 1.2 mol of benzyl alcohol were added, and the reaction mixture was stirred at 60° C. for a further hour. At this time, GC of the reactions indicated a conversion of 100%. After warming to room temperature, 180 ml of water were added and the phases were separated. After the solvent had been condensed out, the product remained in a yield of 96%, HPLC purity 97% (a/a)

Example 4

Rearrangement of octylhydroxamic Acid to tert-butyloxycarbonylheptylamine 1 mol of octylhydroxamic acid and 2 mol of triethylamine were introduced into 50 ml of ethyl acetate and cooled to 0° C. 1.2 mol of T3P solution in ethyl acetate (50% w/w) were metered in while maintaining the reaction temperature, followed by stirring at this temperature for a further three hours. 1.2 mol of tert-butanol were added, and the reaction mixture was stirred at 60° C. for a further hour. At this time, GC of the reactions indicated a conversion of 100%. After warming to room temperature, 180 ml of water were added and the phases were separated. After the solvent had been condensed out, the product remained in a yield of 97%, GC purity 97% (a/a).

The invention claimed is:

1. A method for preparing unprotected or carbamate-protected amines of the formulae (II) and (III),

(II)

or

(III)

comprising reacting hydroxamic acids of the formula (I)

(I)

with
- a.) alkylphosphonic anhydrides,
- b.) an alcohol $R^2OH$ and
- c.) optionally a base, in a reaction solution at a reaction temperature in the range from −100 to +120° C., wherein the hydroxamic acid (1) is generated either before the reaction or during the reaction (in situ), and $R^1$ is an optionally substituted linear or branched $C_1$-$C_{12}$-alkyl radical, substituted $C_3$-$C_{10}$-cycloalkyl, alkenyl, aryl or heteroaryl radicals, and $R^2$ is an allyl, aryl, open-chain, cyclic or branched $C_1$ to $C_{12}$-alkyl radical, an aryloxy, allyloxy or alkoxy radical optionally substituted by open-chain, cyclic or branched $C_1$ to $C_{12}$-alkyl radicals.

2. The method as claimed in claim 1, wherein the phosphonic anhydride is a 2,4,6- substituted 1,3,5,2,4,6-trioxatriphosphinane of the formula (IV)

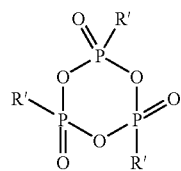
(IV)

in which R' is independently of one another allyl, aryl or open-chain or branched $C_1$ to $C_{12}$-alkyl radicals.

3. The method as claimed in claim 2, wherein R' is a methyl, ethyl, n-propyl, isopropyl, n-butyl, 2-butyl, isobutyl, pentyl, and/or hexyl radical.

4. The method as claimed in claim 1, wherein the phosphonic anhydride is added either as melt or dissolved in a solvent to the reaction solution.

5. The method as claimed in claim 4, wherein the phosphonic anhydride is added in an aprotic solvent.

6. The method as claimed in claim 1, wherein the reaction solution is equilibrated at the reaction temperature before adding the phosphonic anhydride.

7. The method as claimed in claim 1, wherein the amount of the phosphonic anhydride employed is one third stoichiometric to above stoichiometric in relation to the hydroxamic acid (I) based on P equivalents.

8. The method as claimed in claim 1, wherein an amine base $NR^3_3$ is employed as base, where $R^3$ is an allyl, aryl, open-chain, cyclic or branched $C_1$ to $C_{12}$-alkyl radical, an aryloxy, allyloxy or alkoxy radical optionally substituted by open-chain, cyclic or branched $C_1$ to $C_{12}$-alkyl radicals, and $R^3$ in $NR^3_3$ may represent different radicals.

9. The method as claimed in claim 2, wherein R' is an ethyl, propyl and/or butyl radical.

* * * * *

UNITED STATES PATENT AND TRADEMARK OFFICE
CERTIFICATE OF CORRECTION

PATENT NO. : 7,468,460 B2  Page 1 of 1
APPLICATION NO. : 11/995000
DATED : December 23, 2008
INVENTOR(S) : Meudt et al.

It is certified that error appears in the above-identified patent and that said Letters Patent is hereby corrected as shown below:

Title Page
Item (57), Abstract
Line 4, delete "alkylpliosphonic" insert --alkylphosphonic--
Line 6, delete "hydroxainic" insert --hydroxamic--

Signed and Sealed this

Tenth Day of February, 2009

JOHN DOLL
*Acting Director of the United States Patent and Trademark Office*